United States Patent [19]

Pape et al.

[11] Patent Number: 4,726,971
[45] Date of Patent: Feb. 23, 1988

[54] COMPOSITE PRELAMINATED TAPES FOR DIAPER CLOSURES

[75] Inventors: Peter H. K. Pape, Hilden; Jörg O. P. Tuschy, Kerpen, both of Fed. Rep. of Germany

[73] Assignee: Minnesota Mining and Manufacturing Company, St. Paul, Minn.

[21] Appl. No.: 891,131

[22] Filed: Jul. 31, 1986

[51] Int. Cl.[4] .............................. B32B 3/06; B32B 7/02
[52] U.S. Cl. .................................... 428/40; 428/192; 428/212; 428/354; 428/906; 604/390
[58] Field of Search ............... 428/40, 42, 192, 212, 428/352, 354, 906; 604/390

[56] References Cited

U.S. PATENT DOCUMENTS 3,616,114 10/1971 Hamaguchi .......................... 428/41

FOREIGN PATENT DOCUMENTS 3141113 5/1983 Fed. Rep. of Germany .

Primary Examiner—Alexander S. Thomas
Attorney, Agent, or Firm—Donald M. Sell; James A. Smith; Edward T. Okubo

[57] ABSTRACT

Composite prelaminated tape for forming closures for disposable diapers comprising a pressure-sensitive adhesive fastening tape partially overlying a release tape and a unifying strip bridging an edge of the release tape and the adjacent portion of the fastening tape. In use, the fastening tape and the release tape are bonded permanently to opposite sides of one edge of the diaper, the end of the fastening tape overlying the release tape being thereafter lifted free from the release tape and adhered to the opposite edge of the diaper from which it can be respectively reused and re-adhered to the edge of the diaper.

6 Claims, 6 Drawing Figures

COMPOSITE PRELAMINATED TAPES FOR DIAPER CLOSURES

BACKGROUND OF THE INVENTION

This invention relates to composite prelaminated tapes for forming closures for disposable diapers which can be opened and refastened without destroying either the diaper or the tape.

At least as early as 1955, it had been suggested to use strips of normally tacky and pressure-sensitive adhesive tape to hold conventional cloth diapers on a infant; see, e.g., Chambers U.S. Pat. No. 2,714,889 and Ekberg U.S. Pat. No. 3,221,738. A few years later, when disposable diapers became extremely popular, strips of pressure-sensitive adhesive tape were again employed as closures; see, e.g., Gellert U.S. Pat. No. 3,620,217.

A disposable diaper typically has a thin, flexible, stretchy low density polyethylene film cover, an absorbent filler on the inside of the cover, and a porous inner liner overlying the filler. Such a diaper is positioned at the crotch of an infant, the two ends of the diaper extending, respectively, toward the front and back. Adjacent edges of the diaper at each side are then either positioned adjacent to each other or overlapped, a strip of pressure-sensitive adhesive tape being adhered to the cover at the border adjacent each of the two edges and holding the diaper closed.

After a tape closure has been opened, it is frequently discovered that the diaper has not been soiled and hence that there is no need to replace it. If the cover has not been torn, a second strip of tape can sometimes be applied as a replacement closure, but this is often inconvenient. As a result, considerable work has been undertaken to develop a tape diaper closure that is not only capable of bonding firmly to the diaper cover but is also capable of non-destructive removal and replacement. Closures of this type have generally involved a combination of two or more tapes, one of which remains permanently adhered to one edge of the diaper and is removably adhered on the other edge of the diaper. Examples of such products are shown in Ness et al. U.S. Pat. No. 3,951,149, Milnamow U.S. Pat. No. 3,987,793, Feldman et al. U.S. Pat. No. 3,999,546, Richman et al. U.S. Pat. No. 4,020,842 and Schotz U.S. Pat. No. 4,227,530.

Typically, tape closures for diapers are fabricated by a manufacturer of diapers mounting a plurality of individual rolls of the appropriate tapes in his equipment, combining them in situ to form a composite strip of tape, the width of which is substantially the same as the length of the diaper closure to be fabricated. The composite roll is then severed at right angles to the edges of the composite strip at intervals corresponding to the width of the desired tape closure and adhered at an appropriate location along the border adjacent the sides of the diaper as exemplified in Hamaguchi et al. U.S. Pat. No. 3,616,114. Although this manufacturing process is effective, relatively sophisticated machinery is necessary to accomplish the superimposition of several rolls of tape to form a composite strip of tape in situ. Thus, it is desirable to provide diaper manufacturers with a composite prelaminated tape in a single roll from which closures may readily be prepared.

German OS No. 31 41 113 is directed to a seemingly similar adhesive fastening tape for diapers comprising a fastening tape, subdivided into a bonded section and a fastening section, and a release strip. The fastening section is covered with an adhesive layer; the bonded section and the release strip are coated with an adhesive layer having a specific adhesion value five times higher than the specific adhesion value of the adhesive on the fastening section.

BRIEF SUMMARY

The present invention provides novel composite prelaminated tapes for forming closures for disposable diapers of the type comprising a body of fluid-absorbing material having a fluid-impermeable polymeric foil outer cover, with a pressure-sensitive adhesive tape closure permanently mounted at a first border location adjacent one edge of the diaper and adapted for attachment to a second border location adjacent another edge when the two edge locations are juxtaposed or overlapped.

In accordance with the invention, the composite prelaminated tapes for forming the closures comprise a composite of
(a) a pressure-sensitive adhesive fastening tape subdivided into a bonded section and a fastening section,
(b) a release tape,
(c) a fingerlift, and
(d) a unifying strip for distributing tensile forces to both faces of the diaper.

The composite permits a portion of the fastening tape to be adhered permanently to the outer aspect of the diaper at a first border location and the remaining portion of the fastening tape can be lifted from the release tape and adhered to a second border location adjacent the edge and can be repeatedly lifted therefrom and readhered thereto.

Composite closures of the type just described are advantageously prepared from a roll of tape comprising a composite elongate strip of pressure-sensitive adhesive sheet material wound convolutely upon itself about an annular core. This composite strip is especially suited for preparing tape closures of the type described by simply severing the elongate strip of tape parallel to the axis of the core at intervals corresponding to the predetermined width of the closure.

BRIEF DESCRIPTION OF THE DRAWINGS

The invention can be more easily understood by referring to the accompanying drawings, in which certain dimensions are exaggerated to facilitate understanding. Like numbers refer to like parts in the several views, wherein.

DETAILED DESCRIPTION

Figure 1:
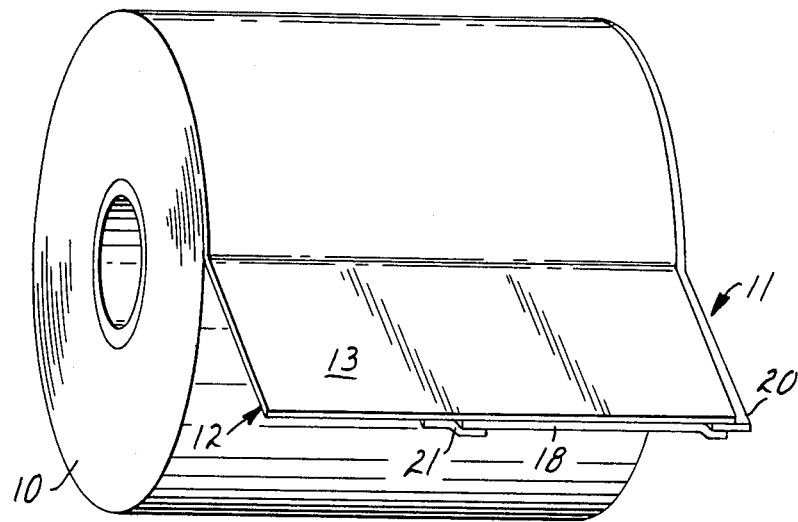
FIG. 1 shows a roll of composite tape suitable for use in practicing the invention.
Figure 2:
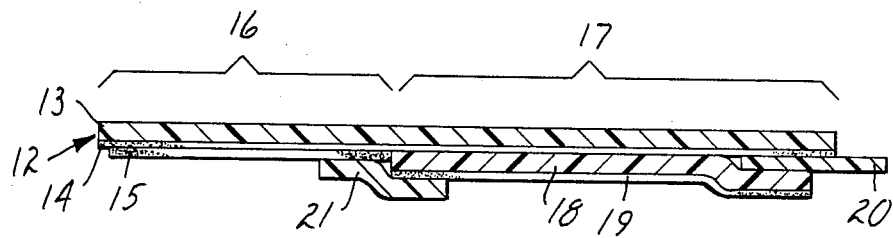
FIG. 2 is an enlarged cross-sectional view of the composite tape of FIG. 1.

Turning first to FIGS. 1 and 2, tape roll 10 is formed of composite tape 11 wound convolutely upon itself about a core. Composite tape 11 is in turn made up of fastening tape 12, subdivided into bonded section 16 and fastening section 17, release tape 18 and unifying strip 21. Fastening tape 12 comprises any suitable tape backing 13 such as treated creped paper, polymeric film, etc., typically provided with a coating of a suitable release agent to facilitate unwinding of the composite tape when wound upon itself about a core. In one embodiment of the invention, one face of the backing 13 is coated with a layer 14 of normally tacky and pressure-sensitive adhesive typically of the so-called "rubber-resin" type. An additional layer 15 of a tacky and aggressive pressure-sensitive adhesive is coated over the layer 14 of normally tacky pressure-sensitive adhesive. The additional layer 15 of tacky and aggressive pressure-sensitive adhesive occupies about one-third of the face area of backing 13 and forms bonded section 16 of composite tape 11. The remaining approximately two-thirds of fastening tape 12 covered only with layer 14 of normally tacky pressure-sensitive adhesive forms the fastening section 17 of fastening tape 12. The adhesive used for layer 14 can be any conventional highly elastomeric and normally tacky pressure-sensitive ahdesive. Suitable adhesives include the conventional rubber-resin adhesives which have their tack characteristics modified by the inclusion of tackifying resins such as those described in U.S. Pat. No. 4,136,071. Useful adhesives for layer 14 are those adhesives having a peel strength between about 4 and 7 newtons per 25 mm, preferably below 6 newtons per 25 mm. The aggressive pressure-sensitive adhesives used for layer 15 include conventional rubber-resin adhesives modified to have peel strengths between about 7 and 10 newtons per 25 mm, preferably about 8 newtons per 25 mm. The difference in peel strengths between adhesive layer 14 and adhesive layer 15 should be at least 1.5 newtons per 25 mm and preferably about 2 newtons per 25 mm. A suitable method for measuring the peel strengths of adhesive layers on a steel, polyethylene or polypropylene surface is described hereinbelow.

DESCRIPTION OF TEST PROCEDURE

90° Peel Adhesion. A 330-micrometer thick sheet of low density polyethylene (e.g., Eastman 1550 P-16421) is cast on a highly polished chrome roll and cooled to room temperature. Test samples approximately 80 mm×300 mm are then cut from this polyethylene sheet and a highly aggressive double-coated pressure-sensitive adhesive tape used to bond the non-shiny surface of the polyethylene to a smooth steel panel. A 25 mm×300 mm specimen of tape to be evaluated as a potential diaper closure is then obtained and the adhesive surface placed in contact with the shiny surface of the polyethylene sheet and forced into intimate contact with one forward and back pass of a mechanically operated 100 g roller. Within one minute thereafter the steel test panel is then mounted in the lower jaw of an "Instron" tensile testing machine with the tape surface upward. The free end of the tape strip is then pulled upward at 90° and mounted in the upper jaw of the tensile testing machine. The upper and lower jaws are separated at a rate of approximately 300 mm/min., noting the average force required for removal.

Release tape 18, formed of any suitable tape backing material, is positioned so that it coincides with and covers and is adhered to adhesive layer 14. The top surface of release tape 18 may, if desired, be provided with a coating of a release agent so that fastening tape 12 may be readily separated from release tape 18 in use.

The other or bottom surface of release tape 18 is coated with a layer 19 of pressure-sensitive adhesive. This adhesive layer 19 must form a strong shear bond to the inner surface of the diaper where it is adhered during use and may be the same as either adhesive layer 14 or 15.

Figure 4:
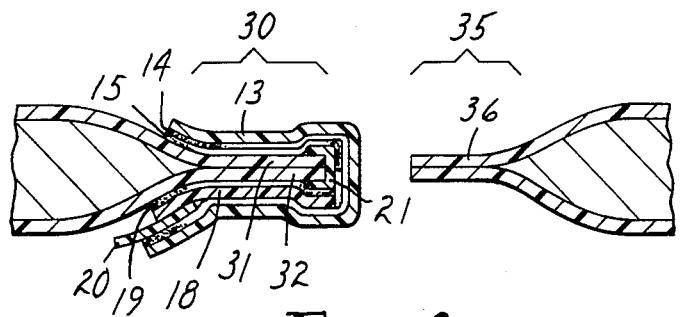
FIG. 4 is a cross-sectional view showing juxtaposed diaper edges, a closure formed from the tape of FIGS. 1 and 2 applied to one of the edges.
Figure 5:
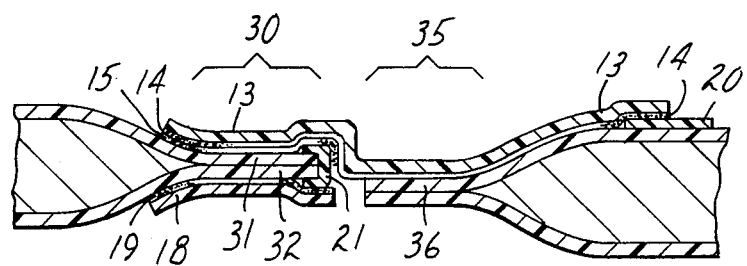
FIG. 5 shows the tape closure in place on the two juxtaposed diaper edges.
Figure 6:
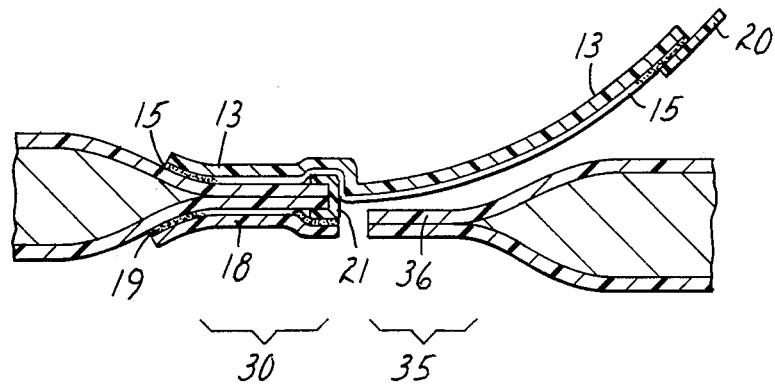
FIG. 6 shows how the tape closure is opened without destroying either the tape or the diaper.

Fingerlift 20, which is typically formed of a narrow strip of any polymeric film, is adhered to adhesive layer 14 at the free end of fastening section 17 and extends outwardly beyond the edge of fastening tape 12 to permit and facilitate the separation of fastening tape 12 from release tape 18 when in the position shown in FIG. 4 and to lift fastening section 17 of fastening tape 12 when it is desired to open the diaper closure (see FIGS. 5 and 6).

Unifying strip 21, typically formed of a narrow strip of the same material as fingerlift 20, is positioned so that its centerline coincides with the junction of adhesive layers 14 and 15 on fastening tape 12. Thus, one-half of unifying strip 21 is adhered to adhesive layer 15 and the other half is adhered to adhesive layer 19 as shown most clearly in FIGS. 2 and 3.

Figure 3:
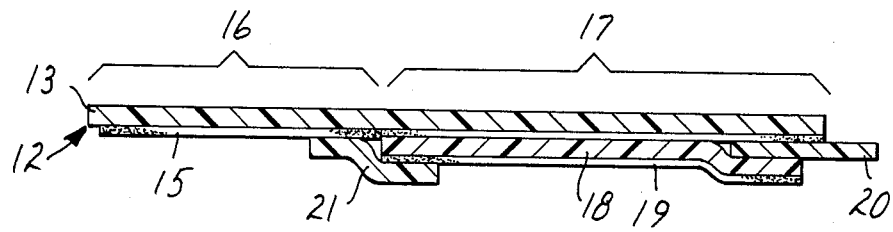
FIG. 3 is an enlarged cross-sectional view of another embodiment of the composite tape of the invention.

The construction of composite tape 11 shown in FIGS. 3 and 6 is essentially the same as that shown in FIG. 2, except that pressure-sensitive adhesive layer 14 does not extend completely across the surface of fastening tape 12 as in FIG. 2 but is coated only over approximately two-thirds of fastening tape 12 to form fastening section 17. Adhesive layer 15 is coated on the remaining one-third of fastening tape 12 and forms bonded section 16.

As previously indicated, FIGS. 4–6 illustrate the use of closures formed by severing composite tape 11 at intervals corresponding to the predetermined width of the closure, parallel to the axis of the tape core. Thus, in FIG. 4, diaper edges 30 and 35 are juxtaposed, surfaces 31 and 36 corresponding to the outer surface of the diaper cover, conventionally made of low density polyethylene foil. As shown in FIG. 4, adhesive layer 15 forming bonded section 16 of fastening tape 12 is adhered to diaper cover 31 in the area immediately adjacent the edge 30. Unifying strip 21 overlies and extends onto outer surface 31 and similarly extends onto interior surface 32 of the diaper. Release tape 18 is permanently adhered to the inner surface 32 of diaper edge 30. Overlying and adhered to the back surface of both unifying strip 21 and release tape 18 is fastening portion 17 of fastening tape 12. Because of the presence of a release agent on the back surface of release tape 18, however, fastening tape 12 can be conveniently removed by grasping fingerlift 20, moving the end of fastening tape 12 through an arc shown, and then adhering it to the outer surface 36 of diaper edge 35, yielding the arrangement shown in FIG. 5.

It will be observed, especially in FIG. 5, that when the diaper edges 30 and 35 are placed in tension such as when a diapered baby moves, the tensional forces places fastening tape 12 in shear. The shear forces on one end of fastening tape 12 are then divided to the top surface 31 and bottom surface 32 of diaper edge 30 through unifying strip 21 due to the adhesive attachment of unifying strip 21 to fastening tape 12 and release tape 18. The division of the shear forces to the two surfaces 31 and 32 of diaper edge 30 substantially diminishes the likelihood of the tape closure being pulled off diaper edge 30 by tearing the cover film forming either surface 31 or 32. The shear forces on the other end of fastening tape 12 are distributed through the extended length of fastening tape 12 over surface 36.

When it is desired to open the diaper closure, the end of fastening tape 12 is lifted free, by grasping fingerlift 20, of diaper surface 36, to which it bonds firmly enough to prevent inadvertent opening of the closure but not so firmly that it cannot be lifted free without tearing diaper cover 36. Once lifted free, this end of fastening tape 12 can again be resealed by placing it in contact with the diaper cover 36; indeed, the process can be successfully repeated several times.

What is claimed is:

1. A roll of tape comprising an elongate prelaminated tape composite wound convolutely upon itself about an annular core, especially suited for preparing a tape closure for disposable diapers by simply severing said elongate prelaminated tape composite parallel to the axis of the core at intervals corresponding to the predetermined width of said closure, the length of each such closure corresponding to the width of the roll of tape, said prelaminated tape composite comprising in combination (a) a fastening tape comprising an elongate strip of sheet backing material, having first and second edges, being substantially as wide as said tape composite, and having a layer of a first normally tacky and pressure-sensitive adhesive coated over substantially one surface of said backing material;

(b) a layer of a second normally tacky and pressure-sensitive adhesive coated over approximately one-third of the layer of said first normally tacky and pressure-sensitive adhesive along the first edge thereof;

(c) a fingerlift adhered to the first pressure-sensitive adhesive adjacent the second edge thereof;

(d) a release tape, having first and second surfaces, the first surface adhered to said first layer of pressure-sensitive adhesive layer;

(e) a layer of normally tacky and pressure-sensitive adhesive coated over the second surface of said release tape; and (f) a unifying strip centered along the junction of sad second adhesive layer and the adhesive layer on said release tape and adhered to said adhesive layers.

2. A roll of tape according to claim 1 wherein said first normally tacky and pressure-sensitive adhesive layer has a peel strength of between about 4 and 7 newtons per 25 mm and said second normally tacky and pressure-sensitive adhesive layer has a peel strength of between about 7 and 10 newtons per 25 mm.

3. A roll of tape according to claim 1 wherein the difference in peel strengths between the first and second normally tacky and pressure-sensitive adhesive layer is at least 1.5 newtons per 25 mm.

4. A roll of tape according to claim 1 wherein said first normally tacky and pressure-sensitive adhesive layer is coated only over approximately two-thirds of the surface of said backing material and said second normally tacky and pressure-sensitive adhesive layer is coated over the remaining approximately one-third of the surface of said backing material.

5. A roll of tape according to claim 1 wherein the layer of normally tacky and pressure-sensitive adhesive layer coated over the second surface of said release tape has a peel strength of between about 4 and 7 newtons per 25 mm.

6. A roll of tape according to claim 1 wherein the layer of normally tacky and pressure-sensitive adhesive layer coated over the second surface of said release tape has a peel strength of between about 7 and 10 newtons per 25 mm.

* * * * *